United States Patent [19]

Pless

[11] Patent Number: 5,425,748
[45] Date of Patent: Jun. 20, 1995

[54] METHOD AND APPARATUS FOR CARDIAC DEFIBRILLATION

[75] Inventor: Benjamin D. Pless, Menlo Park, Calif.

[73] Assignee: Ventritex, Inc., Sunnyvale, Calif.

[21] Appl. No.: 102,437

[22] Filed: Aug. 5, 1993

[51] Int. Cl.$^6$ .............................................. A61N 1/36
[52] U.S. Cl. .............................................. 607/5
[58] Field of Search ...................... 607/4, 5, 7, 14, 25; 128/905

[56] References Cited

U.S. PATENT DOCUMENTS

| | | | |
|---|---|---|---|
| 2,368,207 | 1/1945 | Eaton | 128/697 |
| 3,706,313 | 12/1972 | Milani et al. | |
| 3,924,641 | 12/1975 | Weiss | |
| 4,384,585 | 5/1983 | Zipes | |
| 4,637,397 | 1/1987 | Jones et al. | |
| 4,708,145 | 11/1987 | Tacher, Jr. et al. | |
| 4,768,512 | 9/1988 | Imran | |
| 4,850,357 | 7/1989 | Bach, Jr. | |
| 4,998,531 | 3/1991 | Bocchi et al. | |
| 5,007,422 | 4/1991 | Pless et al. | |
| 5,163,429 | 11/1992 | Cohen | 607/4 |

OTHER PUBLICATIONS

"Ventricular Defibrillation Using Biphasic Waveforms: the Importance of Phasic Duration" (Tang, et al) JACC vol. 13, No. 1, pp. 207–214, Jan. 1989.

Primary Examiner—William E. Kamm
Assistant Examiner—Scott M. Getzow
Attorney, Agent, or Firm—Mark J. Meltzer; Steven M. Mitchell

[57] ABSTRACT

An implantable defibrillator and method for its use are disclosed. Amplified heart signals are fed back to a fibrillating heart to cause defibrillation by creating consistent enhancement and/or interference between the natural electrical signals in the heart and the coherent defibrillation signal. A unipolar endocardial sensing lead positioned in the right ventricular apex provides sensed electrical signals from the heart to a differential amplifier located in an implantable defibrillator. The amplified signal is provided to a sample and hold circuit which is disconnected from the amplifier by a switch during delivery of a defibrillation signal. The amplified heart signal from the sample and hold circuit is conditioned in a linear or non-linear manner and then further amplified by an isolation amplifier. The signal from the isolation amplifier is applied to the heart for periods of on the order of hundreds to thousands of milliseconds. A detector senses the amplitude of the signal at a point between the differential amplifier and the isolation amplifier and discontinues the defibrillation pulses upon detection of reduced cardiac activity for a predetermined period of time.

19 Claims, 2 Drawing Sheets

METHOD AND APPARATUS FOR CARDIAC DEFIBRILLATION

FIELD OF THE INVENTION

The present invention relates generally to devices and methods for controlling heart arrhythmias, and more specifically to an implantable defibrillator and method of delivering defibrillating electrical signals to a patient's heart.

BACKGROUND OF THE INVENTION

A number of different systems and methods have been developed for delivering electrical shocks to a patient's heart in response to detected abnormal heart rhythms (arrhythmias). These methods deliver specific waveform shapes or pulse sequences to the heart in order to treat the detected arrhythmia by depolarizing the heart tissue cells. One early waveform is disclosed in U.S. Pat. No. 3,706,313 to Milani et al., which provides a circuit for delivering a "trapezoidal" wave shape for defibrillating the heart by truncating the output of an exponentially decaying capacitor. Others have suggested the use of sequential pulses delivered through multiple pathways such as described in U.S. Pat. No. 4,708,145 to Tacker, Jr. In Tacker, Jr., a series of rectangular or truncated exponential pulses are delivered to the heart using at least three electrodes where a first pulse is sent through a first pair of the three electrodes and then a second pulse is sent through a second, different pair of the electrodes. Still others have described the use of multiphasic waveforms, such as U.S. Pat. No. 4,637,397 to Jones et al., which describes a triphasic waveform. A triphasic waveform has three pulses of alternating positive and negative polarity. U.S. Pat. No. 3,924,641 to Weiss and U.S. Pat. No. 4,850,357 to Bach, Jr. describe the use of biphasic waveforms.

Defibrillation pulses of the type described above are typically in the range of from 500 to 1000 volts delivered for a time of from about 2 to 10 milliseconds. Overall energy delivery to the heart for a defibrillation waveform may typically be from about 10 to 30 joules.

Another modification of the standard waveform has been suggested by Iraran in U.S. Pat. No. 4,768,512. That patent discloses a cardioverting system (defibrillation and cardioversion) in which a truncated exponential waveform is chopped at high frequencies to provide a voltage wave packet formed of a plurality of high-frequency cardioverting pulses with a preferred frequency in excess of 1 KHz.

Some prior art defibriilators deliver defibrillation shocks to the heart without any correlation or synchronization to the timing of the sensed QRS complex from an electrocardiogram (ECG) while some other prior art devices synchronize such shocks to the QRS complex. Tachyarrhythmias, which are rapid but organized heart rhythms, may be treated with cardioversion pulses. These pulses are similar to defibrillation pulses but generally are delivered at lower voltages and are synchronous with the QRS complex. Pulses are delivered synchronously to help avoid the accelerating a heart experiencing a ventricular tachyarrhythmia into ventricular fibrillation. Such a cardioverter is disclosed in U.S. Pat. No. 4,384,585 to Zipes. In Zipes, an implantable synchronous intracardiac cardioverter detects intrinsic depolarization of cardiac tissue and provides a shock to the heart in synchrony with the detected cardiac activity at a time when the bulk of cardiac tissue is already depolarized and in a refractory state. Synchronizing defibrillating pulses is not required since the heart is already in fibrillation when such pulses are delivered.

A primary goal in treating a detected tachyarrhythmia with an implantable cardioverter/defibrillator is to ensure delivery of effective therapy while minimizing energy delivery requirements for the defibrillation waveform. Lower voltage signals are less painful and disruptive to the patient. Also, lower voltage signals allow for use of smaller batteries and capacitors even where the overall energy delivery is not reduced. Smaller batteries and capacitors result in a smaller implantable defibrillator.

SUMMARY OF THE INVENTION

The present invention provides lower voltage defibrillation signals to depolarize the myocardial cells by feeding back amplified sensed heart signals to create consistent interference between the natural electrical signals in the heart and the synchronized defibrillation signal. The heart is sensed discontinuously in the preferred embodiment but may be sensed continuously in an alternative embodiment. A unipolar endocardial sensing lead positioned in the right ventricular apex provides sensed electrical signals from the heart to a differential amplifier located in an implantable defibrillator. The amplified signal is provided to a sample and hold circuit which is disconnected from the amplifier using a switch during delivery of a defibrillating signal. The signal may then be modified in a non-linear way by an "f(x)" circuit, which in its simplest form is an amplifier, and then further amplified by an isolation amplifier. The signal from the isolation amplifier is applied to the heart for periods of on the order of hundreds to thousands of milliseconds. A detector senses the amplitude of the signal at a point between the differential amplifier and the isolation amplifier and discontinues the defibrillation signal upon detection of reduced cardiac activity for a predetermined period of several hundred milliseconds. By using the coherent amplified heart signal as the waveform for the defibrillation pulse, wavefronts of cardiac depolarization in the axis of the defibrillating leads are consistently enhanced or interfered with resulting in a higher level of cardiac organization which allows defibrillation to occur.

It is therefore an object of the present invention to provide a method and apparatus for delivering defibrillation pulses which requires lower voltage than conventional defibrillation pulses.

It is a further object of the invention to provide a method and apparatus for delivering defibrillation pulses which utilizes the heart's electrical signals to generate a defibrillating pulse.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION OF THE INVENTION

Figure 1:
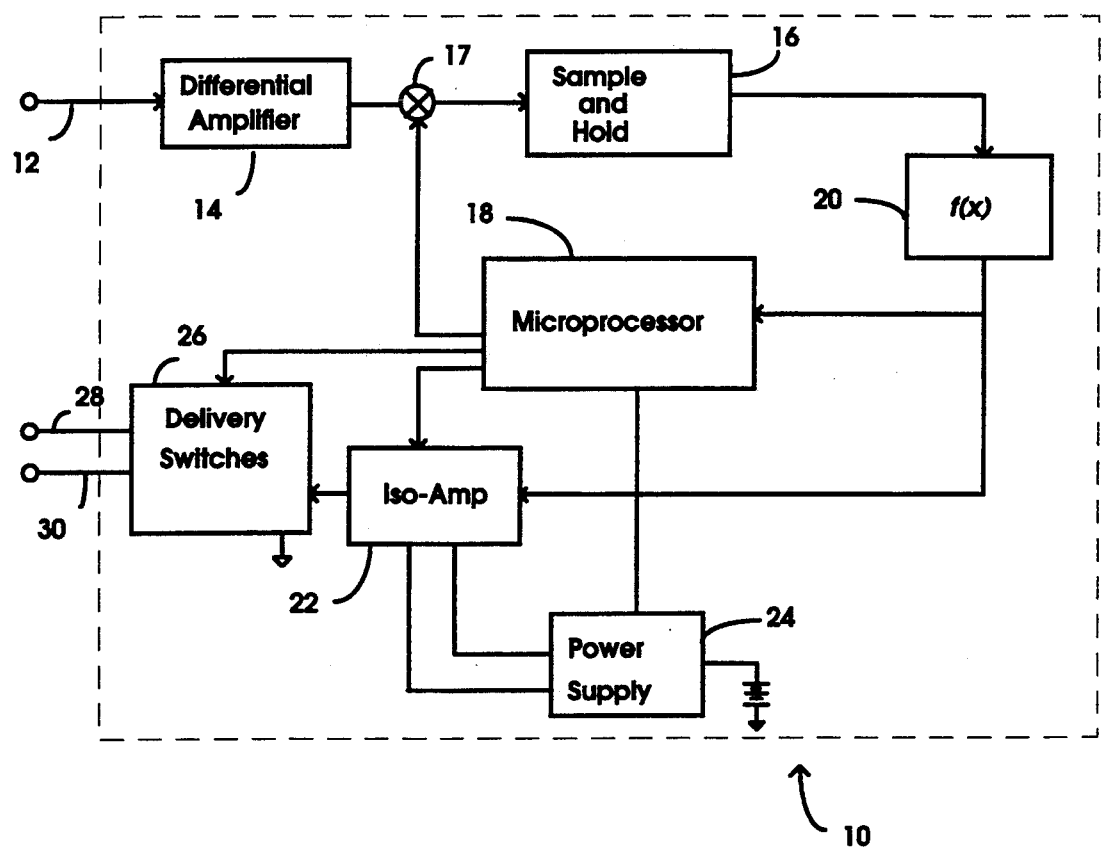
FIG. 1 shows a block diagram of the pulse generation portion of an implantable defibrillator used in connection with the invention.

Referring now to FIG. 1, a block diagram of the pulse generator 10 of the invention is shown. Electrocardiogram (ECG) signals are received from a patient's heart along sensing/pacing lead 12. A sensing/pacing electrode is preferably located at the tip of a unipolar endocardial sensing lead which is positioned in the right ventricular apex of the heart. A bipolar sensing lead may be used but may not be as sensitive to spatial cardiac activity as a unipolar lead. The ECG signal from the sensing/pacing lead 12 is provided to a differential amplifier 14. The input signal to differential amplifier 14 is typically on the order of a few millivolts. The output signal of the differential amplifier 14, which is on the order of one volt (peak), is provided to a sample and hold circuit 16 by a switch 17 under control of a microprocessor 18. This provides a sample of the sensed heart signal when the defibrillation output is not active. The output of the sample and hold circuit 16 is coupled to a conditioning "f(x)" circuit 20 which in one embodiment of the invention may be a linear amplifier. Alternatively, it may operate on the input signal by providing a square law, exponential or other non-linear output, as long as the output is related to the sensed cardiac activity. In an alternate embodiment of the invention, conditioning circuit 20 may be provided with programmable polarity reversal which is used to reverse the polarity of the output stimulating signals to selectively enhance or interfere with the waves of cardiac depolarization.

Microprocessor 18 senses the output of conditioning circuit 20 to detect the signal level and determine when delivery of defibrillating signals should be initiated and terminated. In an alternative embodiment, microprocessor 18 may sense the cardiac activity signal elsewhere such as following the sample and hold circuit 16.

The modified cardiac signal from f(x) circuit 20 is provided to an isolation amplifier 22 which allows isolation between the input power supply and the pulse generator output. Isolation is advantageous because of the difficulties associated with sensing a low level heart signal following a comparatively large amplitude stimulation signal, but is not required. Isolation amplifier 22 receives power from a power supply 24. The gain of isolation amplifier 22 is adjustable under control of microprocessor 18. In the preferred embodiment, the output capacity of isolation amplifier 22 is in the range of plus or minus 50 volts.

Delivery switches 26 are coupled to the output of isolation amplifier 22. These switches are under control of microprocessor 18. There may be a pair of switches or four cross coupled switches to allow polarity reversal of the defibrillation signal. In the preferred embodiment, the switches are implemented using MOS transistors because of their ability to provide very low signal feed through when open. The defibrillation signal is delivered to the heart along a pair of stimulation leads 28, 30. In a preferred embodiment, leads 28 and 30 are endocardial leads with one electrode positioned in the right ventricle (RV) and the other electrode positioned in the superior vena cava (SVC). There may additionally be provided a subcutaneous patch electrode which has the same polarity as either the SVC or RV electrode. Alternatively, leads 28 and 30 may be coupled to epicardial patch electrodes. The endocardial leads allow for greater ease in implanting the system.

In operation, cardiac signals are continuously received and amplified by differential amplifier 14. Sample and hold circuit 16 alternately samples then holds the amplified signal when switch 17 is opened under control of microprocessor 18. During periods of stimulation, the cardiac signal is held in the sample and hold circuit 16 to avoid being corrupted by the stimulation signal. Between stimulation periods, the cardiac signal is acquired by the sample and hold circuit. In a preferred embodiment, a "zero order" sample and hold is used which acquires an instantaneous voltage of the cardiac signal. Alternate types of sample and hold circuits may be used such as ones which average over a sample period, or ones which are higher order so that they can maintain the slope of the cardiac signal during the hold period.

The signal from the sample and hold circuit 16 is then conditioned by conditioning circuit 20 which may simply be an amplifier stage or may provide for more complex conditioning. Proper coherent signal matching of the output stimulation with the heart signals may be provided at this point by providing microprocessor controlled polarity reversal.

Microprocessor 18 receives the output of f(x) circuit 20 and functions as a detector which is used to determine when a defibrillation therapy should be concluded. For example, if the detector input is below a certain predetermined level for a predetermined time, then the defibrillation therapy is considered successful. A typical preselected time for detection of successful defibrillation is on the order of about 300 msec. The fixed level at which the signal threshold is set will depend on the signal amplification by differential amplifier 14 and f(x) circuit 20. The level can be externally programmable or determined by the microprocessor.

Isolation amplifier 22 receives the output of f(x) circuit 20 and generates the cardiac stimulation signal. This signal is essentially an amplified, and perhaps modified, version of the natural heart signal. By using the amplified heart signal as a coherent stimulating signal, wavefronts of cardiac depolarization in the axis of the defibrillating leads are consistently enhanced or interfered with resulting in a higher level of cardiac organization which allows defibrillation to occur. The gain of isolation amplifier 22 is programmable through microprocessor 18 to accommodate different defibrillation requirements. It may be preset for a given patient or change during an episode based on duration or rate of the arrhythmia.

The stimulation signal output of isolation amplifier 22 is provided to delivery switches 26 which are controlled by microprocessor 18. The switches are normally open when no defibrillation therapy is being delivered. During defibrillation therapy, the delivery switches are closed during the hold period of the sample and hold circuit, providing stimulation to the heart. The duration of a stimulation period is on the order of less than 10 msec and may be as short as about 0.1 msec. The acquisition period between stimulation pulses is also short compared to the heart interval but is not necessarily the same as the stimulation interval. The intervals may be predetermined, related to heart activity or random within defined ranges.

Figure 2:
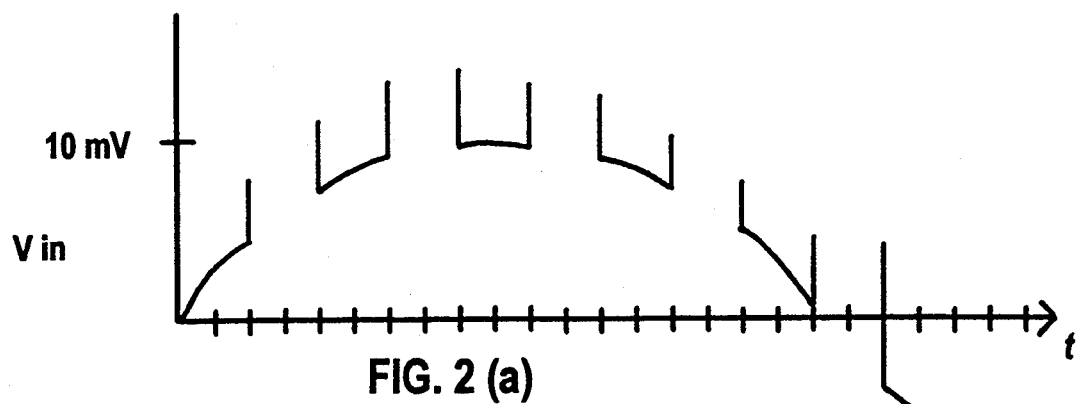
FIGS. 2(a)–2(c) show a sample of the sensed heart signal, the digital logic for the sample and hold circuit, and the coherent output signal used to stimulate the patient's heart.
Figure 2:
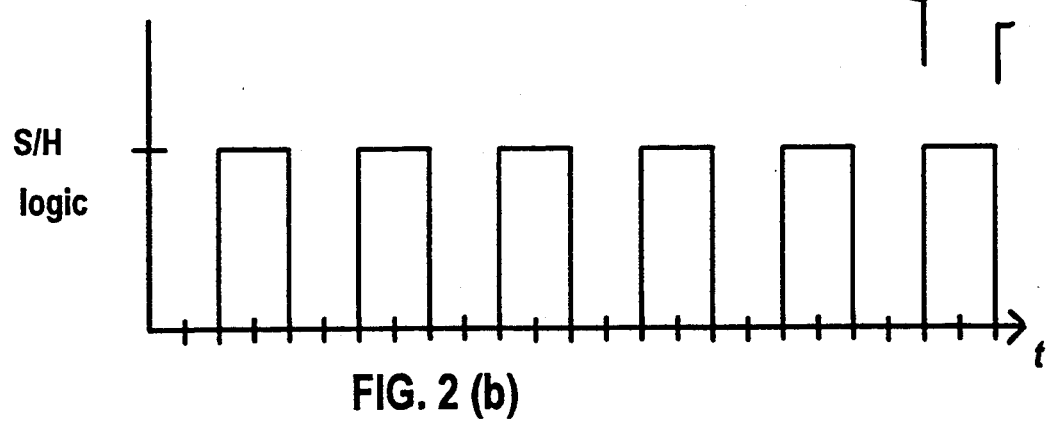
Figure 2:
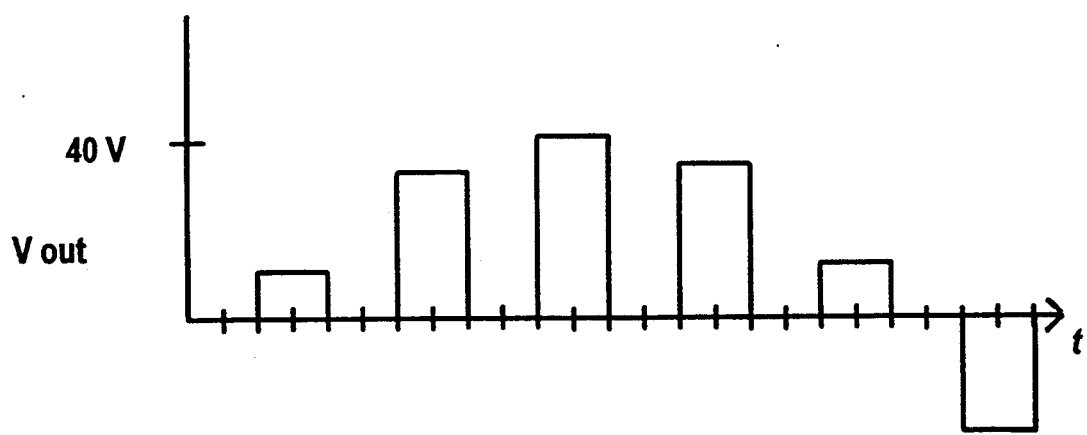

FIG. 2(a) shows a plot of voltage versus time for a typical input signal from the sensing/pacing lead 12 during delivery of defibrillation therapy. The baseline of the signal is the ECG signal on a somewhat expanded time scale with the defibrillation signal pulses saturating the 10 millivolt voltage scale. FIG. 2(b) shows a logic plot for the sample and hold circuit 16 which controls the capture of signals from the ECG. This timing is essentially the opening and closing of switch 17 which is opened, i.e., in a hold state, during the defibrillation signal delivery and closed, i.e., in a sample state, when the defibrillation signal is not being delivered. FIG. 2(c) shows the pulse waveform stimulation signal which is delivered to the heart after the signal from the sample and hold circuit has been conditioned by conditioning circuit 20 and amplified by isolation amplifier 22. This output is controlled through delivery switches 26 by microprocessor 18. Delivery switches 26 are synchronized with switch 17 so that when delivery switches 26 are closed, switch 17 is open.

The preferred embodiment described provides discontinuous stimulation of the heart. An alternative embodiment provides continuous stimulation by adding a high frequency low amplitude signal to the amplified heart waveform. This signal is a marker that is used to subtract the amplified signal from the underlying heart waveform so that the heart waveform can be detected in the presence of the much larger stimulating signal.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A medical device for electrically stimulating a patient's heart comprising:
   a sensing lead for sensing electrical signals of said patient's heart;
   a first amplifier coupled to receive an input signal from said sensing lead and adapted to provide an amplified output signal;
   a sample and hold circuit for sampling said amplified output signal and holding it in memory;
   a second amplifier coupled to receive said amplified output signal from said sample and hold circuit memory and further amplify it; and
   pulse delivery means adapted to be coupled to said patient's heart for delivering said further amplified signal.

2. A medical device according to claim 1 and further including a conditioning circuit coupled between said sample and hold circuit and said second amplifier for conditioning an output of said sample and hold circuit.

3. A medical device according to claim 2 wherein said conditioning circuit is an amplifier.

4. A medical device according to claim 2 wherein said conditioning circuit provides an output which is a non-linear function of its input.

5. A medical device according to claim 1 and further including a microprocessor for controlling the operation of said medical device.

6. A medical device according to claim 5 wherein said microprocessor includes means for detecting the signal level at a point between the output of said first amplifier and the input of said second amplifier.

7. A medical device according to claim 1 wherein said pulse delivery means includes a plurality of delivery switches and at least two defibrillation leads.

8. A medical device according to claim 7 wherein said at least two defibrillation leads are endocardial leads.

9. A medical device according to claim 7 wherein said at least two defibrillation leads are epicardial patch leads.

10. An implantable pulse generator for electrically stimulating a patient's heart comprising:
    a sensor for sensing electrical signals of said patient's heart;
    an amplifier coupled to receive an input signal from said sensor and adapted to provide an amplified output signal;
    a sample and hold circuit coupled to receive said amplified output signal from said amplifier and provide a further output signal following a time delay; and
    delivery means adapted to be coupled to said patient's heart for delivering said further output signal.

11. An implantable pulse generator according to claim 10 and further including a conditioning circuit coupled between said sample and hold circuit and said delivery means for conditioning said further output signal.

12. An implantable defibrillator system for providing coherent defibrillation stimulation to a patient's heart comprising:
    an endocardial sensing lead adapted to be positioned in the right ventricular apex of said patient's heart;
    a differential amplifier having its input coupled to said sensing lead;
    a sample and hold circuit coupled to an output of said differential amplifier;
    an isolation amplifier coupled to an output of said sample and hold circuitry;
    a detector coupled to receive an output signal of either said differential amplifier or said sample and hold circuit;
    delivery switch means coupled to an output of said isolation amplifier;
    pulse delivery leads coupled to said delivery switch means having at least a pair of electrodes adapted to be positioned proximate said patient's heart; and
    a controller responsive to said detector coupled to said delivery switch means for delivering amplified heart signals to the heart through said pulse delivery leads in response to a sensed arrhythmia.

13. A method for treating a tachyarrhythmia comprising the steps of:
    detecting a tachyarrhythmia from a patient's heart;
    sensing an electrical signal from said patient's heart;
    amplifying said sensed signal; and
    applying said amplified electrical signal to said patient's heart.

14. The method of claim 13 wherein said sensing, amplifying and applying steps are sequentially repeated and further including the step in said sequence of sampling said sensed electrical signal and then holding it in memory during each applying step.

15. The method of claim 14 and further including the step of monitoring the level of said amplified sensed electrical signal and discontinuing said applying step when said amplified sensed electrical signal falls below a predetermined threshold for a predetermined time.

16. The method of claim 14 and further including the step of conditioning the sensed heart signal after the step of sampling and holding said signal.

17. The method of claim 16 wherein said conditioning step includes modifying the signal in a non-linear manner.

18. The method of claim 13 and further including the step of conditioning the sensed heart signal after the step of sampling and holding said signal.

19. The method of claim 18 wherein said conditioning step includes modifying the signal in a non-linear manner.

* * * * *